(12) United States Patent
Liu et al.

(10) Patent No.: US 11,173,220 B2
(45) Date of Patent: Nov. 16, 2021

(54) COMPOSITION COMPRISING CATALASE, PREPARATION METHOD AND USE THEREOF AND METHOD FOR KILLING TUMOR CELLS

(71) Applicant: JE & NA BIOTECH. CO., LTD., Suzhou (CN)

(72) Inventors: Zhuang Liu, Suzhou (CN); Kai Yang, Suzhou (CN); Yu Chao, Suzhou (CN); Qi Zhao, Suzhou (CN)

(73) Assignee: JE & NA BIOTECH. CO., LTD., Suzhou (CN)

( * ) Notice: Subject to any disclaimer, the term of this patent is extended or adjusted under 35 U.S.C. 154(b) by 0 days.

(21) Appl. No.: 16/606,976

(22) PCT Filed: Jun. 19, 2018

(86) PCT No.: PCT/CN2018/091841
§ 371 (c)(1),
(2) Date: Oct. 21, 2019

(87) PCT Pub. No.: WO2018/233605
PCT Pub. Date: Dec. 27, 2018

(65) Prior Publication Data
US 2020/0384136 A1   Dec. 10, 2020

(30) Foreign Application Priority Data
Jun. 22, 2017 (CN) .......................... 201710467595.5

(51) Int. Cl.
*A61K 51/08* (2006.01)
*A61P 35/00* (2006.01)
*A61K 9/16* (2006.01)
*A61K 9/00* (2006.01)
*A61K 45/06* (2006.01)

(52) U.S. Cl.
CPC ............ *A61K 51/08* (2013.01); *A61K 9/1652* (2013.01); *A61K 9/1658* (2013.01); *A61P 35/00* (2018.01); *A61K 9/0019* (2013.01); *A61K 45/06* (2013.01); *C12Y 111/01006* (2013.01)

(58) Field of Classification Search
None
See application file for complete search history.

(56) References Cited

U.S. PATENT DOCUMENTS

| | | | |
|---|---|---|---|
| 7,951,921 B2 | 5/2011 | Hansen et al. | |
| 8,313,896 B2 * | 11/2012 | Martuza | A61K 39/0011 435/5 |
| 2002/0156033 A1 * | 10/2002 | Bratzler | A61K 39/00119 514/44 R |
| 2004/0057950 A1 * | 3/2004 | Waksal | A61P 35/00 424/141.1 |
| 2005/0226905 A1 * | 10/2005 | Tien | A61K 9/1652 424/439 |
| 2009/0123406 A1 | 5/2009 | Pheiffer | |
| 2015/0132279 A1 | 5/2015 | Kageyama et al. | |

FOREIGN PATENT DOCUMENTS

| | | |
|---|---|---|
| CA | 2842306 A1 | 1/2013 |
| CN | 103040727 A | 4/2013 |
| CN | 104271145 A | 1/2015 |
| CN | 105012959 A | 11/2015 |
| CN | 107213479 A | 9/2017 |
| EP | 3 643 315 A1 | 4/2020 |
| WO | WO 2002/49501 A2 | 6/2002 |
| WO | WO 2003/106495 A2 | 12/2003 |
| WO | WO 2014/126537 A1 | 8/2014 |
| WO | WO 2018/233605 A1 | 12/2018 |

OTHER PUBLICATIONS

Hayashi et al., "Smart Ferrofluid with Quick Gel Transformation in Tumors for MRI-Guided Local Magnetic Thermochemotherapy," Advanced Functional Materials, vol. 26, Issue 11, pp. 1708-1718 (2016).
Huang et al., "An Implantable Depot That Can Generate Oxygen in Situ for Overcoming Hypoxia-Induced Resistance to Anticancer Drugs in Chemotherapy," Journal of the American Chemical Society, pp. 1-5 (2016).
Song et al., "Catalase-Loaded TaOx Nanoshells as Bio-Nanoreactors Combining High-Z Element and Enzyme Delivery for Enhancing Radiotherapy," Advanced Materials, pp. 1-6 (2016).
International Search Report for Application No. PCT/CN2018/091841 dated Sep. 10, 2018.
Chinese Office Action for Application No. 201710467595.5 dated Sep. 10, 2018.
International Preliminary Report on Patentability and Written Opinion for Application No. PCT/CN2018/091841 dated Dec. 24, 2019.
European Search Report for Application No. 18819947 dated Feb. 17, 2021.

* cited by examiner

Primary Examiner — Yunsoo Kim
(74) Attorney, Agent, or Firm — Jenkins, Wilson, Taylor & Hunt P.A.

(57) ABSTRACT

A composition comprising catalase, a preparation method and a use thereof, and a method for killing tumor cells are provided. The composition comprises a radionuclide labeled to a biomacromolecule, a soluble alginate and catalase. The composition can be injected into the tumor through an interventional treatment. A gel is formed when an alginate ion in the composition enters the tumor and encounters a calcium ion, such that the radionuclide and the catalase are uniformly confined in the tumor. The composition comprising catalase utilizes catalase to decompose dissolved oxygen generated from hydrogen peroxide in the tumor to advance the hypoxic state of the tumor cells, and the tumor cells are killed with radiation after the hypoxic state thereof has been advanced, and thus the invention has good prospects for applications in cancer therapy.

14 Claims, 5 Drawing Sheets

COMPOSITION COMPRISING CATALASE, PREPARATION METHOD AND USE THEREOF AND METHOD FOR KILLING TUMOR CELLS

CROSS-REFERENCE TO RELATED APPLICATIONS

The present application is a national stage application under 35 U.S.C. 371 based on international patent application PCT/CN2018/091841, filed on Jun. 19, 2018 which claims the priority of Chinese Patent Application No. 201710467595.5 filed on Jun. 22, 2017, the disclosures of both of which are incorporated in the present application by reference in their entireties.

TECHNICAL FIELD

The present disclosure relates to the field of medical technology, and in particular to a composition for preparing an anti-tumor agent and use thereof, and specifically to a composition comprising catalase, a preparation method and use thereof and a method for killing tumor cells.

BACKGROUND

Radionuclides have different enrichment effects in different organ tissues. For example, thyroid cells have a special affinity for iodide. After oral administration of a certain amount of iodine-131, the most of them can be absorbed by the thyroid gland. When iodine-131 decays into xenon-131, β-rays (99%) and γ-rays (1%) are emitted. The former has an effective range of 3.63 mm and an average range of 0.48 mm, which can selectively destroy the thyroid acinar epithelium without affecting adjacent tissues. However, the enrichment effects of radionuclides limit their application to other tissues. In the prior art, minimally-invasive implantation of radioactive particles is one of the currently ideal methods. The radioactive material is placed in a microcarrier, which is then implanted at the lesion under the guidance of ultrasound or CT in a minimally-invasive surgery. The tumor cells will be killed by the radiation emitted upon particle decay. In this way, the carrier particles will remain in the patient's body permanently, which will have long-term effects on the patient's body. In addition, this implantation method has problems such as uneven distribution and poor coverage, which is difficult to achieve a desired effect.

On the other hand, hypoxia is found in most of the human solid tumors due to the disordered growth of tumors and insufficient angiogenesis. The ability of tumor cells in hypoxic state to resist ionizing radiation is several times higher than that of normal oxygenated tumor cells because the damage of DNA by oxygen radicals is reduced. Therefore, the radiation has a limited killing effect on hypoxic tumor cells, resulting in an in-apparent therapeutic effect of the existing radiation particles.

SUMMARY

The present disclosure provides a composition comprising catalase, a preparation method and use thereof and a method for killing tumor cells. The composition can relieve the hypoxia in tumor cells, increase the uniformity of the distribution of radioactive particles and the ability of radiative rays to kill tumor cells without affecting the surrounding normal tissues.

To achieve at least one of the above purposes of the present disclosure, the present disclosure may employ the following technical solutions:

The disclosure provides a catalase-comprising composition, which comprises catalase, a soluble alginate, and a radionuclide labeled on a bio-macromolecule.

A gel is formed when the alginate ions in the composition enter into the tumor and encounter calcium ions, and adheres to the inside of the tumor, such that the radionuclide-labeled bio-macromolecules and catalase are uniformly confined within the tumor. The catalase can decompose hydrogen peroxide in the tumor to produce dissolved oxygen, thereby relieving the hypoxia in tumor cells. In addition, the radioactive rays can ionize the dissolved oxygen to generate oxygen free radicals which can kill tumor cells, thereby greatly enhancing the killing effect of radioactive rays on tumor cells.

On the other hand, the soluble alginate, catalase and radionuclide-labeled bio-macromolecules can form a network-like uniformly-distributed gel structure according to the internal structure of the tumor. The catalase and radionuclide-labeled bio-macromolecules are confined in the gel structure formed from the alginate due to their suitable physical structure without being carried by the blood to the patient's normal tissue area, thereby reducing the overall dosage of radionuclides while ensuring the intensity of radiative rays in the lesion area. In addition, the alginate gradually degrades within a few weeks in organisms, leaving no particles.

Optionally, in the composition comprising catalase, the soluble alginate includes at least one selected from the group consisting of sodium alginate, potassium alginate, ammonium alginate and propylene glycol alginate. After the soluble alginate is dissolved into a solution, the alginate ions in the solution will crosslink with calcium ions to form a three-dimensional network-like gel. Sodium alginate is a natural polysaccharide which has the stability, solubility and viscosity required for adjuvants of pharmaceutical preparations.

Optionally, in the composition comprising catalase, the soluble alginate is potassium alginate, wherein potassium ions promote the contraction of blood vessels and reduce the fluidity of the injected fluid in tumors.

Optionally, in the composition comprising catalase, the soluble alginate is a mixture of sodium alginate and potassium alginate. The proportion in the mixture can be adjusted according to the different conditions of the blood vessels in the tumor, thereby adjusting the contraction degree of the blood vessels and adjusting the distribution state of the composition in the blood vessels.

Optionally, in the composition comprising catalase, the radionuclide includes at least one selected from the group consisting of iodine-131, iodine-125, phosphorus-32, yttrium-90, gallium-67, indium-111, thallium-201, palladium-203, bismuth-213, actinium-225, lutecium-177, rhenium-186, palladium-212 and rhenium-188. In the lesion area, radionuclides kill and inhibit tumor cells by utilizing their radioactivity.

Optionally, in the composition comprising catalase, the radionuclide is iodine-131 or iodine-125.

Optionally, in the composition comprising catalase, the radionuclide-labeled bio-macromolecule is at least one selected from the group consisting of a protein, a nucleic acid and a polysaccharide. The bio-macromolecules of the present disclosure are bio-macromolecules well known in the art and are useful as carriers for radionuclides, including enzymes and serum proteins.

Optionally, in the composition comprising catalase, the radionuclide is labeled on the catalase. The uniformity of the relative distance distribution between the radiation and the dissolved oxygen generated by the catalase can be further defined by labeling a radionuclide on the catalase, such that no non-uniform spatial distribution is occurred as a result of the differences in molecular weight. Thereby, the generation probability of oxygen free radicals and their killing effects on tumor cells are increased.

Optionally, in the composition comprising catalase, the concentration of the catalase is 5 mg/mL-10 mg/mL, the concentration of the alginate is 5 mg/mL-10 mg/mL and the dose of the radionuclide is 200 Ci/mL-500 Ci/mL. Alginate at a concentration of 5 mg/mL to 10 mg/mL has a good gelation ability, which allows the composition to spread well within the tumor. If the alginate has a concentration of less than 5 mg/mL, it's gelation ability is insufficient, and the composition is likely to flow out of the tumor. If the alginate has a concentration of more than 10 mg/mL, it gels too fast, causing the composition to stay in a certain part of the tumor. Both cases affect the efficacy of the composition.

Optionally, in the composition comprising catalase, the composition further comprises an immune-stimulating agent.

Optionally, in the composition comprising catalase, the immune-stimulating agent includes at least one selected from the group consisting of CpG oligodeoxynucleotide which is an immunologic adjuvant, R837, TLR7 agonists, TLR8 agonists, NLR agonists, STING agonists, MPLA (Monophosphoryl Lipid A), LPS, PGNs, R848, G100, SD-101, MGN1703, CMP-001, FLA, polyU, poly(dT), CL307, CL264, CL097, CL075, MEDI9197, MEDI5083, hypoxanthine and MDP. Cytokine includes IL-1, IL-1α, IL-1β, IL-2, IL-2 superkine, IL-6, IL-7, IL-9, AM0010, IL-12, IL-15, IL-15 superagonist, ALT-803, NIZ985, IL-16, IL-18, IL-21, denenicokin, IL-12 superagonist antibody, IFN-α, IFN-β, IFN-γ, TNF-α, GM-GSF, RG7461, RG7813, M9241, etc. The immune-stimulating agent may be used in combination with antibodies against immune checkpoint blockers such as an antibody against cytotoxic T lymphocyte-associated antigen-4 (Anti-CTLA-4), Anti-PD-1, Anti-PD-L1, etc. and costimulatory signal molecules such as Anti-TIM3, Anti-OX40, Anti-GITR, Anti-LAG-3, Anti-CD137, Anti-CD27, Anti-CD28, Anti-CD28H, Anti-CD39, Anti-CD40, Anti-CD47, Anti-CD48, Anti-CD70, Anti-CD73, Anti-CD96, Anti-CD160, Anti-CD200, Anti-CD244, etc. to produce suitable amount of antigens for immune therapy. The addition of an immunologic adjuvant to the composition results in a better production of tumor-associated antigens. Then the use of an antibody against the immune checkpoint blocker for immune response modulation facilitates to kill distal tumors or metastases by utilizing the autoimmune. Thus, the distal tumors or metastases are treated while treating in situ tumors.

The present disclosure provides a method for preparing a composition comprising catalase, comprising mixing an alginate solution, a radionuclide and catalase.

Optically, the ratio of the amount of the alginate, the catalase, and the radionuclide is 5 mg-10 mg: 5 mg-10 mg: 200 Ci-500 Ci.

Optically, the alginate solution, radionuclide and catalase are mixed by a method comprising mixing an alginate solution with radionuclide-labeled catalase.

Further, as an implementation, the radionuclide-labeled catalase is prepared by a method comprising mixing a radionuclide, an oxidizing agent and a dispersion medium, and mixing the obtained mixture with a bio-macromolecule such as catalase and serum proteins, then shaking, standing, washing and separating. The radionuclide is mixed with the oxidizing agent for oxidation, which gives the radionuclide a stronger electrophilic substitution capability. The oxidizing agent includes chloramine-T, and the dispersion medium includes at least one selected from the group consisting of physiological saline and phosphate buffered saline (PBS).

As another implementation, the radionuclide-labeled catalase is prepared by a method comprising mixing catalase with a chelating agent and then dialyzing to obtain chelated catalase; mixing a radionuclide with the chelated catalase and a reducing agent, followed by ultrafiltration purification. A chelating agent is used in this method such that a chelating agent capable of chelating radioactivity is present on the catalase, i.e., the catalase is modified on the surface with a chelating agent capable of labeling a radionuclide. The radionuclide is then chelated with the chelating agent by using a reducing agent to obtain radionuclide-labeled catalase. In the present disclosure, the chelating agent includes DTPA-based and DOTA-based chelating agents, and the reducing agent includes sodium borohydride or potassium borohydride.

The present disclosure provides the use of the above-described composition comprising catalase for the preparation of an anti-neoplastic agent.

Optically, the use comprises use of the composition in combination with at least one selected from the group consisting of an antibody against cytotoxic T-lymphocyte-associated antigen-4, anti-PD-1 and anti-PD-L1. Suitable amount of antigens is produced for immune therapy, and distal tumors or metastases are killed by utilizing the autoimmune. Thus, the distal tumors or metastases are treated while treating in situ tumors.

The present disclosure also provides a method for killing tumor cells. The above composition is injected into a tumor by means of interventional treatment. A network-like cross-linked gel structure is formed according to the internal structure of the tumor when the alginate ions in the composition enter into the tumor and encounter calcium ions, and adheres to the inside of the tumor, such that the radionuclides labeled on bio-macromolecules and catalase are uniformly coated and confined within the tumor. The catalase can decompose hydrogen peroxide in the tumor to produce dissolved oxygen, thereby relieving the hypoxia in tumor cells. The rays generated by the radionuclides can kill tumor cells in which the hypoxia has been relieved.

Optionally, prior to interventional treatment, the calcium concentration in blood or in tumors and surrounding tissue regions is adjusted.

Advantages of the present disclosure include:

In the present disclosure, a gel is formed from alginate ions and calcium ions, and adheres to the inside of the tumor, such that the radionuclide-labeled bio-macromolecules and catalase are uniformly confined within the tumor. The catalase can decompose hydrogen peroxide in the tumor to produce dissolved oxygen, thereby relieving the hypoxia in tumor cells. In addition, the radioactive rays can ionize the dissolved oxygen to generate oxygen free radicals to kill tumor cells, thereby greatly enhancing the killing effect of radioactive rays on tumor cells. Thereby, the problem of radiation resistance of hypoxic tumor cells existing in the prior art is solved.

The network-like uniformly-distributed gel structure formed from the alginate ions and calcium ions defines the uniformity of the relative distance distribution between the radiative rays and the dissolved oxygen generated by the catalase, thereby improving the problems in the prior art that the non-uniform distribution and poor coverage of radionuclides that has been placed in carrier particles in advance will occur after being implanted into the lesion area.

In addition, the composition may be used in combination with an antibody against cytotoxic T lymphocyte antigen-4 (CTLA-4) to treat both in situ tumors and distal or metastatic tumors because antigens may be generated when killing tumor cells.

BRIEF DESCRIPTION OF THE DRAWINGS

The present disclosure is further described below in conjunction with the accompanying drawings and embodiments.

DETAILED DESCRIPTION

Figure 1:
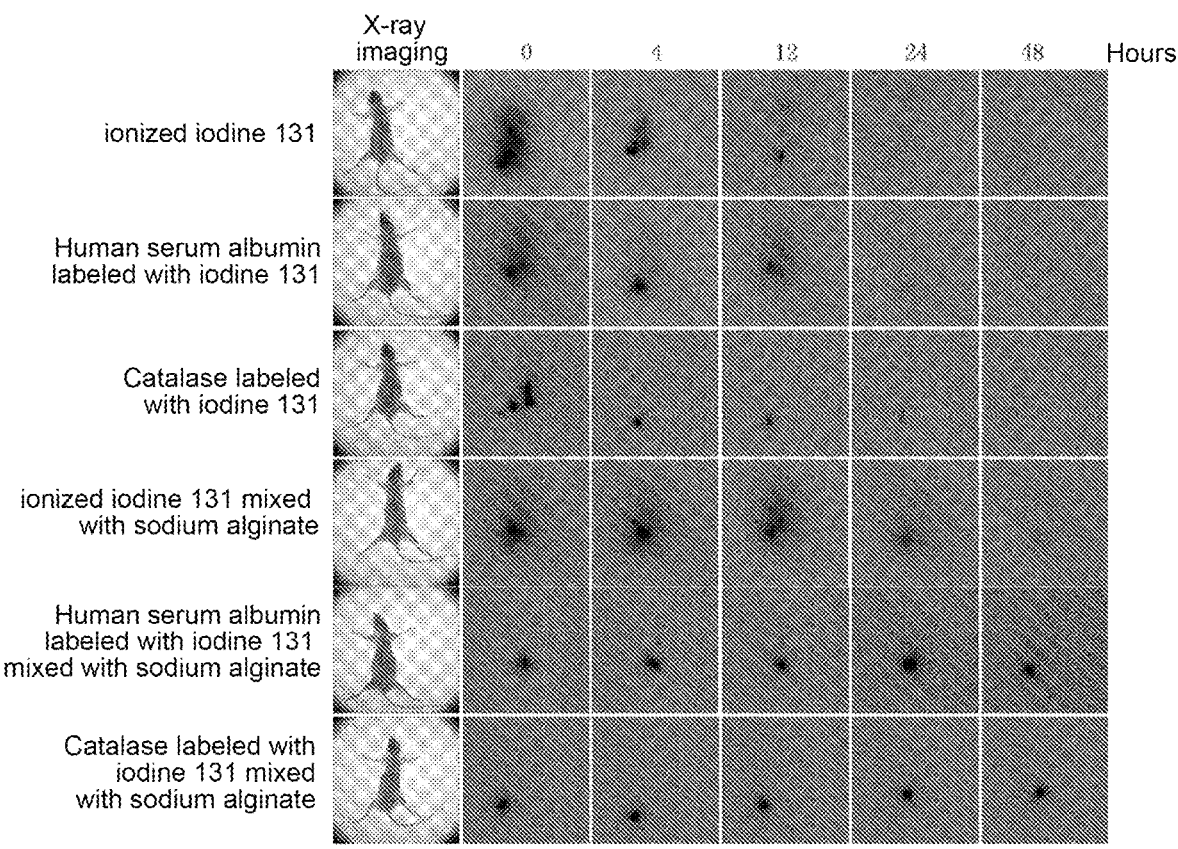
FIG. 1 is a graph showing the imaging to monitor the movement of radionuclides in mouse tumors within 48 h in Test Example 1.

The technical solutions in the embodiments of the present disclosure will be clearly and completely described below in order to clarify the objects of the examples, the technical solutions and the advantages of the present disclosure. The examples which are not indicated with specific conditions are carried out according to the conventional conditions or the conditions recommended by the manufacturer. The reagents or instruments for use, which are not indicated with manufacturers, are conventional products that are commercially available.

The present disclosure is described in detail below with reference to the examples and the accompanying drawings. However, the following examples are not to be considered as limitations to the scope of the present disclosure.

Example 1

Preparation of a sodium alginate solution: 50 mg of sodium alginate was weighed and dissolved in 10 ml of deionized water, and fully shaken to sufficiently dissolve the sodium alginate to obtain a 5 mg/ml sodium alginate solution.

Preparation of iodine-125-labeled catalase: 550 μl of iodine-125 stock solution and 100 μl of 0.1 mg/ml chloramine-T were mixed, and 500 μl of dispersion medium was added, then the mixture of iodine-125 and chloramine-T was added to 500 μl of 5 mg/ml catalase, shaken and mixed on a vortex shaker for 5 minutes, then allowed to stand at room temperature for 15 minutes. 15 minutes later, the mixture was transferred into a 15 ml ultrafiltration tube and centrifuged at 4000 rpm for 15 minutes, washed 3 times with dispersion medium, then the supernatant was taken out and measured for activity with an activity meter.

The sodium alginate solution and the iodine-125-labeled catalase were uniformly mixed to obtain a composition comprising catalase, wherein the concentration of catalase was 5 mg/mL, the concentration of sodium alginate was 5 mg/mL and the dose of radionuclide was 200 Ci/mL.

Example 2

Preparation of a sodium alginate solution: 75 mg of sodium alginate was weighed and dissolved in 10 ml of deionized water, and fully shaken to sufficiently dissolve the sodium alginate to obtain a 7.5 mg/ml sodium alginate solution.

Preparation of iodine-125-labeled catalase: 550 μl of iodine-125 stock solution and 100 μl of 0.1 mg/ml chloramine-T were mixed, and 500 μl of dispersion medium was added, then the mixture of iodine-125 and chloramine-T was added to 500 μl of 5 mg/ml catalase, shaken and mixed on a vortex shaker for 5 minutes, then allowed to stand at room temperature for 15 minutes. 15 minutes later, the mixture was transferred into a 15 ml ultrafiltration tube and centrifuged at 4000 rpm for 15 minutes, washed 3 times with dispersion medium, then the supernatant was taken out and measured for activity with an activity meter.

The sodium alginate solution and the iodine-125-labeled catalase were uniformly mixed to obtain a composition comprising catalase, wherein the concentration of catalase was 7.5 mg/mL, the concentration of sodium alginate was 7.5 mg/mL and the dose of radionuclide was 350 Ci/mL.

Example 3

Preparation of a sodium alginate solution: 100 mg of sodium alginate was weighed and dissolved in 10 ml of deionized water, and fully shaken to sufficiently dissolve the sodium alginate to obtain a 10 mg/ml sodium alginate solution.

Preparation of iodine-125-labeled catalase: 550 μl of iodine-125 stock solution and 100 μl of 0.1 mg/ml chloramine-T were mixed, and 500 μl of dispersion medium was added, then the mixture of iodine-125 and chloramine-T was added to 500 μl of 5 mg/ml catalase, shaken and mixed on a vortex shaker for 5 minutes, then allowed to stand at room temperature for 15 minutes. 15 minutes later, the mixture was transferred into a 15 ml ultrafiltration tube and centrifuged at 4000 rpm for 15 minutes, washed 3 times with dispersion medium, then the supernatant was taken out and measured for activity with an activity meter.

The sodium alginate solution and the iodine-125-labeled catalase were uniformly mixed to obtain a composition comprising catalase, wherein the concentration of catalase was 10 mg/mL, the concentration of potassium alginate was 10 mg/mL and the dose of radionuclide was 500 Ci/mL.

Example 4

Preparation of a potassium alginate solution: 550 mg of potassium alginate was weighed and dissolved in 10 ml of deionized water, and fully shaken to sufficiently dissolve the potassium alginate to obtain a 55 mg/ml potassium alginate solution.

Preparation of iodine-125-labeled catalase: 550 μl of iodine-125 stock solution and 100 μl of 0.1 mg/ml chloramine-T were mixed, and 500 μl of dispersion medium was added, then the mixture of iodine-125 and chloramine-T was added to 500 μl of 5 mg/ml catalase, shaken and mixed on a vortex shaker for 5 minutes, then allowed to stand at room temperature for 15 minutes. 15 minutes later, the mixture was transferred into a 15 ml ultrafiltration tube and centrifuged at 4000 rpm for 15 minutes, washed 3 times with dispersion medium, then the supernatant was taken out and measured for activity with an activity meter.

The potassium alginate solution and the iodine-125-labeled catalase were uniformly mixed to obtain a composition comprising catalase, wherein the concentration of catalase was 5 mg/mL, the concentration of potassium alginate was 55 mg/mL and the dose of radionuclide was 200 Ci/mL.

Example 5

Preparation of a sodium alginate solution: 75 mg of sodium alginate was weighed and dissolved in 10 ml of deionized water, and fully shaken to sufficiently dissolve the sodium alginate to obtain a 7.5 mg/ml sodium alginate solution.

Preparation of iodine-131-labeled catalase: 50 μl of iodine-131 stock solution and 100 μl of 0.1 mg/ml chloramine-T were mixed, and 500 μl of PBS or physiological saline was added, then the mixture of iodine-131 and chloramine-T was added to 500 μl of 5 mg/ml catalase, shaken and mixed on a vortex shaker for 5 minutes, then allowed to stand at room temperature for 15 minutes. 15 minutes later, the mixture was transferred into a 15 ml ultrafiltration tube and centrifuged at 4000 rpm for 15 minutes, washed 3 times with dispersion medium, then the supernatant was taken out and measured for activity with an activity meter.

The sodium alginate solution and the iodine-131-labeled catalase were uniformly mixed to obtain a composition comprising catalase, wherein the concentration of catalase was 5 mg/mL, the concentration of potassium alginate was 7.5 mg/mL and the dose of radionuclide was 200 Ci/mL.

Example 6

Preparation of a potassium alginate solution: 100 mg of potassium alginate was weighed and dissolved in 10 ml of deionized water, and fully shaken to sufficiently dissolve the potassium alginate to obtain a 10 mg/ml potassium alginate solution.

Preparation of iodine-131-labeled catalase: 50 μl of iodine-131 stock solution and 100 μl of 0.1 mg/ml chloramine-T were mixed, and 500 μl of PBS or physiological saline was added, then the mixture of iodine-131 and chloramine-T was added to 500 μl of 5 mg/ml catalase, shaken and mixed on a vortex shaker for 5 minutes, then allowed to stand at room temperature for 15 minutes. 15 minutes later, the mixture was transferred into a 15 ml ultrafiltration tube and centrifuged at 4000 rpm for 15 minutes, washed 3 times with dispersion medium, then the supernatant was taken out and measured for activity with an activity meter.

The potassium alginate solution and the iodine-131-labeled catalase were uniformly mixed to obtain a composition comprising catalase, wherein the concentration of catalase was 10 mg/mL, the concentration of potassium alginate was 10 mg/mL and the dose of radionuclide was 500 Ci/mL.

Example 7

Preparation of a sodium alginate solution: 50 mg of sodium alginate was weighed and dissolved in 10 ml of deionized water, and fully shaken to sufficiently dissolve the sodium alginate to obtain a 5 mg/ml sodium alginate solution.

1 ml of catalase (50 mg/ml) was mixed with 1 mL of NHS-DTPA (1 μg/ml) for one hour, and then dialyzed against water for one day by using a dialysis bag with a molecular weight cut-off of 3000 to obtain DTPA-catalase.

Preparation of technetium-99-labeled catalase: Technetium-99 (200 μci) was mixed and shaken with DTPA-catalase and 1 μg of sodium borohydride for 10 minutes, and purified by ultrafiltration to obtain technetium-99-labeled catalase.

The sodium alginate solution and the technetium-99-labeled catalase were uniformly mixed to obtain a composition comprising catalase, wherein the concentration of catalase was 5 mg/mL, the concentration of sodium alginate was 5 mg/mL and the dose of radionuclide was 200 Ci/mL.

Example 8

Preparation of a sodium alginate solution: 100 mg of sodium alginate was weighed and dissolved in 10 ml of deionized water, and fully shaken to sufficiently dissolve the sodium alginate to obtain a 10 mg/ml sodium alginate solution.

2 ml of catalase (50 mg/ml) was mixed with 1 mL of NHS-DTPA (1 μg/ml) for one hour, and then dialyzed against water for one day by using a dialysis bag with a molecular weight cut-off of 3000 to obtain DTPA-catalase.

Preparation of rhenium-188-labeled catalase: Rhenium-188 (500 μci) was mixed and shaken with DTPA-catalase and 1 μg of sodium borohydride for 10 minutes, and purified by ultrafiltration to obtain rhenium-188-labeled catalase.

The sodium alginate solution and the rhenium-188-labeled catalase were uniformly mixed to obtain a composition comprising catalase, wherein the concentration of catalase was 10 mg/mL, the concentration of sodium alginate was 10 mg/mL and the dose of radionuclide was 500 Ci/mL.

Comparative Example 1

Preparation of a sodium alginate solution: 50 mg of sodium alginate was weighed and dissolved in 10 ml of deionized water, and fully shaken to sufficiently dissolve the sodium alginate to obtain a 5 mg/ml sodium alginate solution.

Preparation of sodium alginate-combined ionized iodine-131: 50 μL of the iodine-131 stock solution was mixed with 5 mg/ml sodium alginate solution.

Comparative Example 2

Preparation of a sodium alginate solution: 50 mg of sodium alginate was weighed and dissolved in 10 ml of deionized water, and fully shaken to sufficiently dissolve the sodium alginate to obtain a 5 mg/ml sodium alginate solution.

Preparation of iodine-131-labeled human serum albumin: 50 μl of iodine-131 stock solution and 100 μl of 0.1 mg/ml chloramine-T were mixed, and 500 μl of dispersion medium was added, then the mixture of iodine-131 and chloramine-T was added to 500 μl of 5 mg/ml human serum albumin, shaken and mixed on a vortex shaker for 5 minutes, then allowed to stand at room temperature for 15 minutes. 15 minutes later, the mixture was transferred into a 15 ml ultrafiltration tube and centrifuged at 4000 rpm for 15 minutes, washed 3 times with dispersion medium, then the supernatant was taken out and measured for activity with an activity meter.

The sodium alginate solution, iodine-131-labeled human serum albumin and catalase solution were uniformly mixed to obtain a composition comprising catalase, wherein the concentration of catalase was 5 mg/mL, the concentration of alginate was 5 mg/mL and the dose of radionuclide was 200 Ci/mL.

Test Example 1

FIG. 1 is a graph showing the imaging to monitor the movement of radionuclides in mouse tumors within 48 h. A series of experiments were performed on mice to verify that the alginate gel can confine the radionuclide labeled on the bio-macromolecule within the tumor.

Wherein the concentration of sodium alginate was 5 mg/mL, the concentration of catalase was 5 mg/mL and the dose of iodine 131 was 200 Ci/mL. The dispersion medium was PBS solution, and 50 µl was injected into each mouse. 6 breast cancer-bearing mice were divided into 6 groups and intratumorally injected with:

A: ionized iodine-131;
B: iodine-131-labeled human serum albumin;
C: the iodine-131-labeled catalase from Example 6;
D: the sodium alginate-combined ionized iodine-131 as provided in Comparative example 1
E: the sodium alginate-combined iodine-131-labeled human serum albumin as provided in Comparative example 2
F: the sodium alginate-combined iodine-131-labeled catalase as provided in Example 6.

The movement of the injected composition was observed with a Small Animal Radionuclide Imager at 0, 4, 12, 24 and 48 h after the intratumoral injection. The movement of sodium alginate and iodine 131-labeled catalase was monitored in real time by using the radiative rays emitted by iodine 131 nuclide after the direct injection into mouse tumors. As can be seen from FIG. 1, in the control group without sodium alginate, the composition had substantially leaked out of the tumor and been metabolized from the mouse through an intravenous route at 24 hours after injection. However, the sodium alginate effectively retained the iodine-131-labeled bio-macromolecules within the tumor. Thus, it was indicated that a gel was formed when the sodium alginate was injected into the tumor and encountered trace amounts of calcium irons in the tumor, and the gel effectively coated the bio-macromolecules and confined them within the tumor.

Test Example 2

Figure 2:
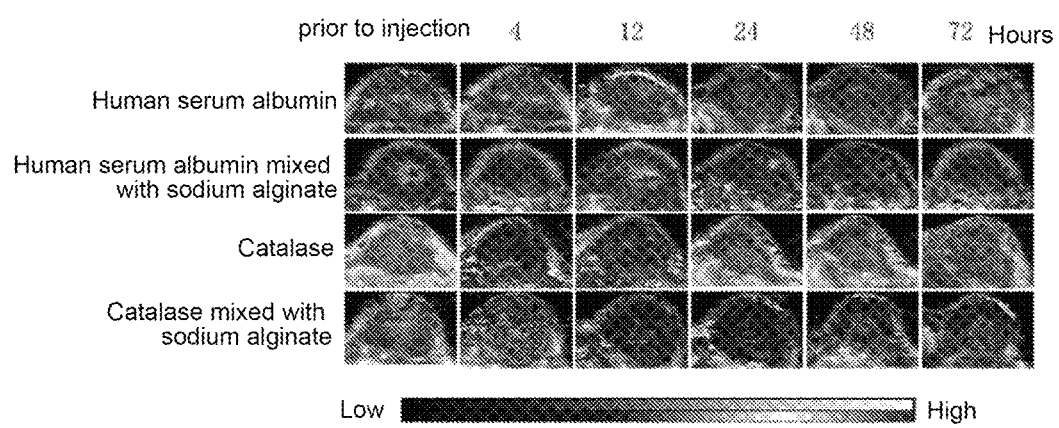
FIG. 2 is a graph showing the photoacoustic imaging to monitor the oxygen concentration in the blood of mouse tumors.

FIG. 2 is a graph showing the photoacoustic imaging to monitor the oxygen concentration in the blood of mouse tumors. The upper legend is a legend of photoacoustic imaging, and the lower legend is a legend of ultrasound imaging. The ability of the composition comprising catalase to relieve hypoxia in the mouse 4T1 tumor models was further verified. 4 breast cancer-bearing mice were intratumorally injected with human serum albumin, catalase, sodium alginate-combined human serum albumin, and sodium alginate-combined catalase respectively. Photoacoustic was used to monitor the oxygen concentration in the blood of tumors. The gray part in the figure showed the shape of the tumor detected by ultrasound imaging, and the white part showed the distribution of dissolved oxygen. It can be seen from FIG. 2 that the combination of sodium alginate and catalase relieved tumor hypoxia for a long time. Due to the presence of the sodium alginate gel, the catalase was well fixed within the tumor, thereby obtaining a long-term hypoxia-relieving effect.

Test Example 3

Figure 3:
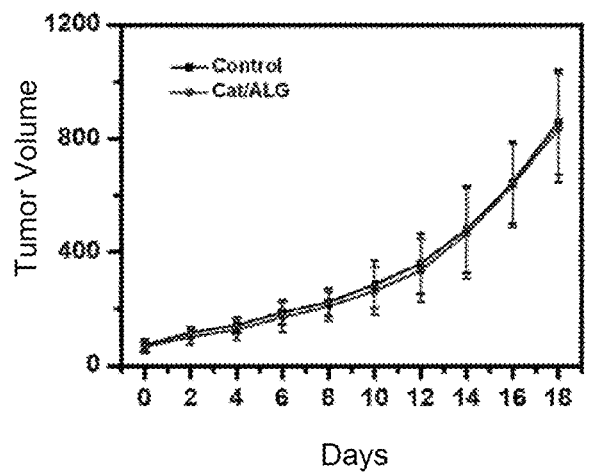
FIG. 3 is a graph showing the tumor growth curve in Test Example 3.

The breast cancer-bearing mice were divided into 2 groups with 5 mice in each group and subjected to parallel experimental treatments. The 2 groups of mice were intratumorally injected with physiological saline and a composite of catalase and sodium alginate respectively. After the intratumoral injection, the length and width of the tumor were measured with a vernier caliper every two days, and the volume of the tumor was calculated as (length×(width× width))÷2. FIG. 3 is a graph showing tumor growth curves and mouse survival curves. It can be seen that the composite of catalase and sodium alginate had no killing effect on tumor tissues at the test concentration.

Test Example 4

Figure 4:
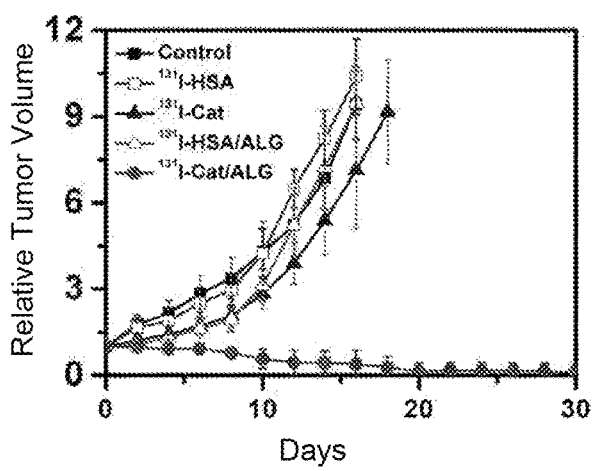
FIG. 4 is a graph showing the tumor growth curve in Test Example 4.
Figure 5:
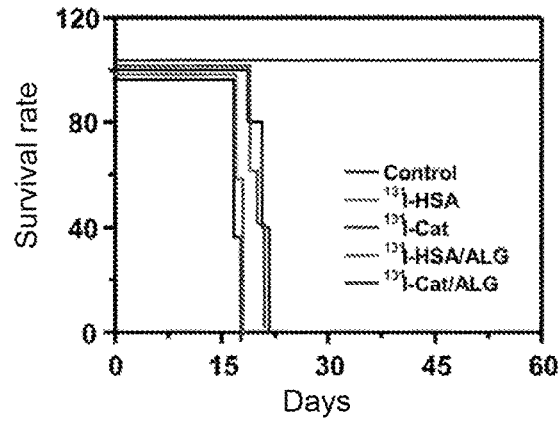
FIG. 5 is a graph showing the mouse survival curve in Test Example 4.

FIG. 4 and FIG. 5 were graphs showing the tumor growth curves of mice and the survival curves of mice, respectively.

The breast cancer-bearing mice were divided into 5 groups with 5 mice in each group and subjected to parallel experimental treatments. The 5 groups of mice were intratumorally injected with physiological saline, iodine-131-labeled human serum albumin, iodine-131-labeled catalase, the sodium alginate-combined iodine-131-labeled human serum albumin as provided in Comparative example 2 and the sodium alginate-combined iodine-131-labeled catalase as provided in Example 6 respectively. After the intratumoral injection, the length and width of the tumor were measured with a vernier caliper every two days, and the volume of the tumor was calculated as (length×(width× width))÷2. It can be seen from the tumor growth curves and the mouse survival curves (FIG. 3 and FIG. 4) that the system enhanced the therapeutic ability of iodine-131, exhibiting a good therapeutic effect. In addition, the mice in the experimental group using a combination of sodium alginate and catalase survived for the longest time. Wherein, "control" represented a control group wherein physiological saline alone was injected and no therapeutic effect was shown; "131I-HAS" represented human serum albumin labeled with iodine 131 alone, wherein only the therapeutic effect of iodine 131 was shown; "131I-Cat" represented iodine 131-labeled catalase, wherein the therapeutic effect of iodine 131 after hypoxia relief was shown; "131I-HSA/ ALG" represented sodium alginate-combined iodine131-labeled human serum albumin; and finally, "131I-Cat/ALG" represented sodium alginate-combined iodine 131-labeled catalase.

Test Example 5

Figure 6:
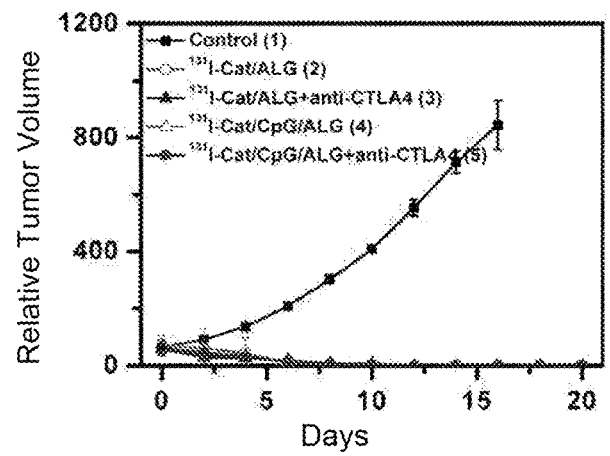
FIG. 6 is a graph showing the in situ tumor growth curve.
Figure 7:
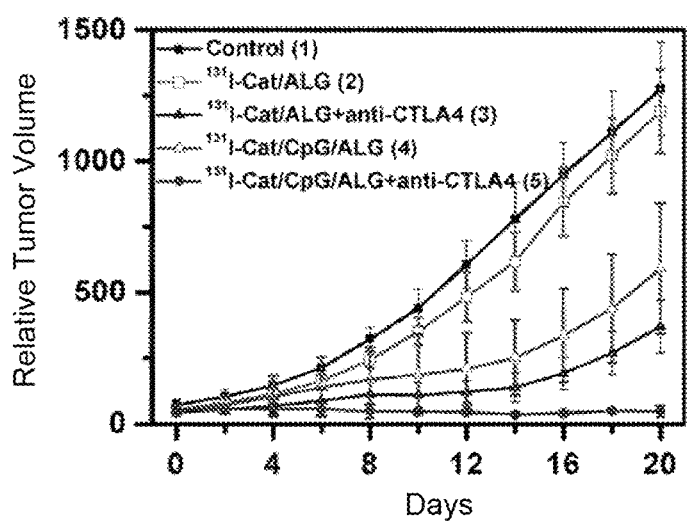
FIG. 7 is a graph showing the distal tumor growth curve.

FIG. 6 and FIG. 7 were graphs showing the in situ tumor growth curves and distal tumor growth curves of mice, respectively.

The tumor-bearing mice inoculated with mouse colon cancer on both sides of the buttocks were divided into 5 groups with 5 mice in each group, and subjected to treatment involving combined immunotherapy. The 5 groups of mice were intratumorally injected respectively with A physiological saline;

B the sodium alginate-combined iodine 131-labeled catalase as provided in Example 6;

C the sodium alginate-combined iodine 131-labeled catalase as provided in Example 6 in combination with an antibody against cytotoxic T-lymphocyte-associated antigen-4. Specifically, the sodium alginate-mixed iodine 131-labeled catalase was injected into the in situ tumor, and the antibody against cytotoxic T lymphocyte-associated antigen-4 was intravenously administered into the body.

D a composition of the sodium alginate-combined iodine 131-labeled catalase as provided in Example 6 and CpG oligonucleotide. At the time of injection, the sodium alginate-combined iodine 131-labeled catalase was directly mixed with the CpG oligonucleotide composition and injected in situ into the tumor.

E a composition of the sodium alginate-combined iodine 131-labeled catalase as provided in Example 6 and CpG oligonucleotide in combination with an antibody against cytotoxic T-lymphocyte-associated antigen-4. The injection was performed as follows: the sodium alginate-combined iodine 131-labeled catalase was directly mixed with the CpG oligonucleotide composition and injected in situ into the tumor, and the antibody against cytotoxic T lymphocyte-associated antigen-4 was intravenously administered into the body.

After the intratumoral injection into the in situ tumor, the length and width of the in situ tumor and the distal tumor were measured with a vernier caliper every two days, and the volume of the tumor was calculated as (length×(width×width))÷2. As can be seen from the in situ tumor growth curves and the distal tumor growth curves (FIG. 5 and FIG. 6), an internal radiotherapy realized by the sodium alginate-combined iodine-131-labeled catalase effectively and almost completely eliminated in situ tumors, which resulted in the generation of related antigens. Thus, when the composition was used in combination with an immune-stimulating nucleotide and an antibody against cytotoxic T lymphocyte-associated antigen-4, the distal tumors were effectively inhibited, thereby achieving a completed treatment of cancer.

Test Example 6

After 20 days of treatment, blood was collected from the mouse eyeballs and the mouse tumors were collected by dissection. The collected blood was allowed to stand at room temperature for 1.5 h and then centrifuged at 3000 rpm for 20 minutes to separate the serum. Immune-related cytokines in serum and tumors were measured by enzyme-linked immunosorbent assay.

Figure 8:
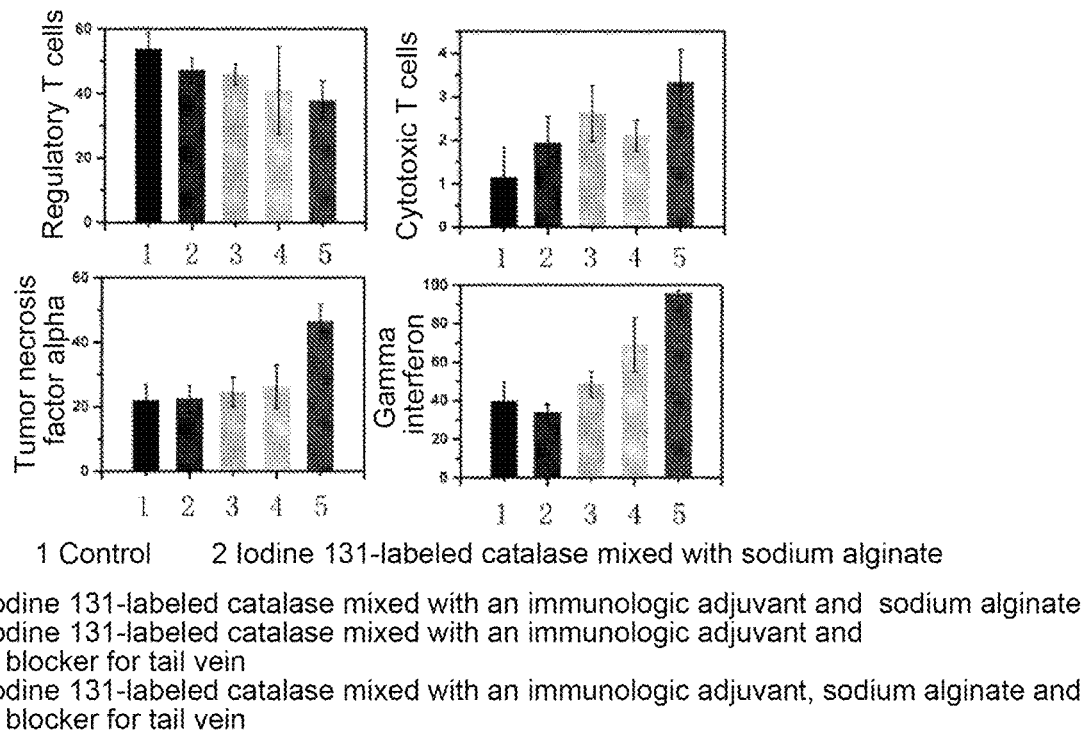
FIG. 8 is a graph showing the content of immune-related cytokines in mice.

As can be seen from FIG. 8, compared with the four control groups A, B, C and D, because the mice in the key experimental group were intratumorally injected with a composition of sodium alginate, iodine-131-labeled catalase and an immunologic adjuvant oligonucleotide and intravenously administered with anti-cytotoxic T lymphocyte-associated antigen 4, the in situ tumors were eliminated by the internal radiotherapy and a large number of related antigens was generated. In addition, related immune factors such as cytotoxic T cells were increased and regulatory T cells were reduced in mice as a result of the combination with an immunologic adjuvant and an immune-stimulating agent, indicating that lymphocytes with tumor-killing properties were increased and lymphocytes that protected tumors were reduced in mice. Further detection of cytokines in distal tumors revealed that gamma interferon was increased accordingly which also indicated that tumor-killing lymphocytes within tumors were increased, and that tumor necrosis factor alpha was increased which indicated that the distal tumors were severely necrotic by lymphocyte challenge. This series of phenomena indicated that the combination use of an immunologic adjuvant and an immune-stimulating agent significantly increased the tumor-killing lymphocytes in mice after the removal of in situ tumors with internal radiotherapy, and these lymphocytes recognized and attacked distal tumor cells in mice and made them necrotic, which convincingly explained the good effect of internal radiotherapy combined with immunotherapy.

Test Example 7

Figure 9:
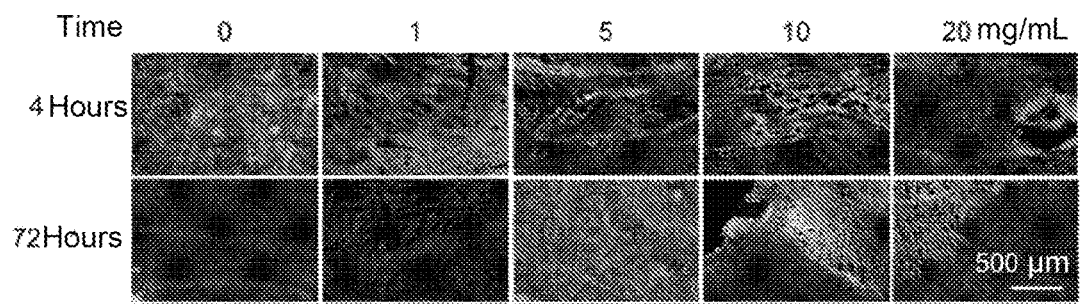
FIG. 9 is a graph showing sections showing the permeation behavior of sodium alginate of different concentrations in tumors.

The penetration behavior of different concentrations of sodium alginate in mouse tumors were further investigated. The catalase was labelled with fluorescein dye as follows: 10 μl of fluorescein dye was added to 1 ml of 5 mg/ml catalase, then 10 mg of 1-ethyl-(3-dimethylaminopropyl)carbodiimide hydrochloride was added, stirred for 12 hours, then 1.1 ml of the reaction solution was transferred to dialysis bag having a molecular weight cut-off of 14800 and dialyzed against water for two days, and water was changed every 12 hours. After dialysis, fluorescein dye-labeled catalase was obtained. The catalase was mixed with different concentrations of sodium alginate (1, 5, 10, and 20 mg/ml), and injected intratumorally into tumors of tumor-bearing mice. Tumors were collected at 4 hours and 72 hours, respectively, and tumor sections were stained. As can be seen from FIG. 9, the sodium alginate at a concentration of 5 mg/ml had a suitable gelation ability and allowed the composition to spread well within the tumor, compared to that at a concentration of less than 5 mg/ml which had an insufficient gelation ability and caused the composition to flow out of the tumor at 72 hours, and that at a concentration of more than 10 mg/ml which gelled too fast and caused the composition to stay in a certain part of the tumor. In summary, it can be concluded that 5-10 mg/ml was the optimum concentration of sodium alginate. The concentration of calcium ions in mice is in the range of $1.5*10-3~1.8*10-3M$, and the concentration in human body is in the range of $1.5*10-3~1.8*10-3M$ too, so the concentration of sodium alginate for the human body is also 5 to 10 mg/ml.

Test Example 8

Figure 10:
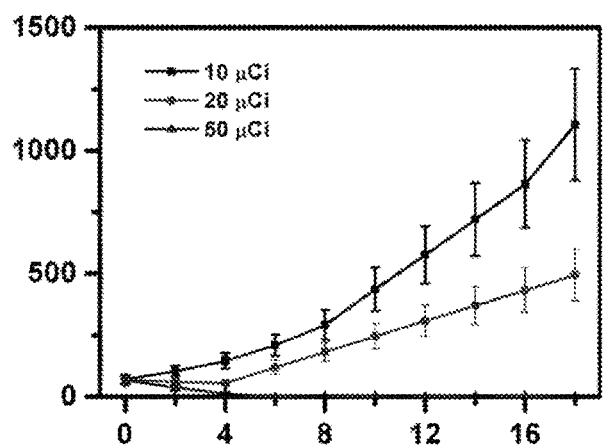
FIG. 10 is a graph showing the tumor growth curve in Test Example 8.

FIG. 10 was a graph showing the tumor growth curve of mice.

The breast cancer-bearing mice were divided into 3 groups with 5 mice in each group and subjected to parallel experimental treatments. The 3 groups of mice were intratumorally injected with a composition of catalase labeled by different doses of iodine 131 and sodium alginate, wherein the dose of iodine 131 was 10, 20 and 50 microcuries respectively. After the intratumoral injection, the length and width of the tumor were measured with a vernier caliper every two days, and the volume of the tumor was calculated as (length×(width×width))÷2. It can be seen from the tumor growth curve (FIG. 10) that the tumor transplantation effect of the composition was gradually relieved as the dose of iodine 131 increased, and 50 μCi of iodine 131 eliminated the tumors in mice completely.

Test Example 9

Figure 11:
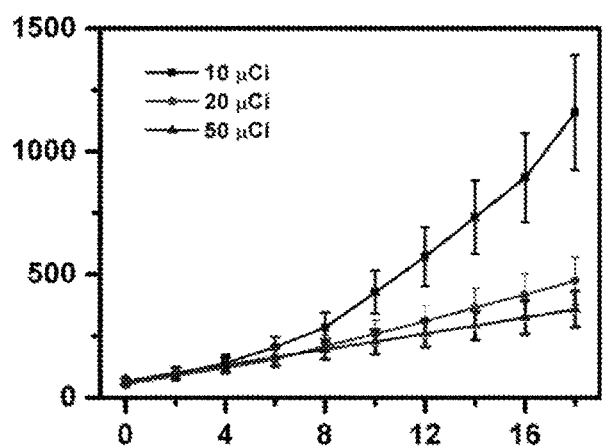
FIG. 11 is a graph showing the tumor growth curve in Test Example 9.

FIG. 11 was a graph showing the tumor growth curve of mice.

The breast cancer-bearing mice were divided into 3 groups with 5 mice in each group and subjected to parallel experimental treatments. The 3 groups of mice were intratumorally injected with a composition of catalase labeled by different doses of iodine 125 and sodium alginate, wherein the dose of iodine 125 was 10, 20 and 50 microcuries respectively. After the intratumoral injection, the length and width of the tumor were measured with a vernier caliper every two days, and the volume of the tumor was calculated as (length×(width×width))÷2. It can be seen from the tumor growth curve (FIG. 11) that the tumor transplantation effect of the composition was gradually increased as the dose of iodine 125 increased, and 50 μCi of iodine 125 had the best therapeutic effect.

In addition, it should be understood that although the description is described in terms of the embodiments, not each embodiment includes only one independent technical solution. The description of the specification is merely for the sake of clarity, and those skilled in the art should regard the specification as a whole. The technical solutions in the respective examples may also be combined appropriately to form other embodiments that can be understood by those skilled in the art. All other examples obtained by those general skilled in the art under the premise of no creative work, on the basis of examples of the present disclosure, are within the scope of the present disclosure.

INDUSTRIAL APPLICABILITY

The present disclosure provides a composition comprising catalase, a preparation method and use thereof and a method for killing tumor cells. The composition utilizes catalase to decompose hydrogen peroxide in the tumor to produce dissolved oxygen, thereby relieving the hypoxia in tumor cells; solving the problems in the prior art involving the radiation resistance of hypoxic tumor cells; increasing the uniformity of the distribution of radioactive particles and the ability of radiative rays to kill tumor cells; improving the problems in the prior art that the non-uniform distribution and poor coverage of radionuclides that has been placed in carrier particles in advance will occur after being implanted into the lesion area, without affecting the surrounding normal tissues. The composition has good prospects for tumor therapy applications.

What is claimed is:

1. A composition, comprising catalase, a soluble alginate, and a radionuclide labeled on the catalase, wherein the soluble alginate includes at least one selected from the group consisting of sodium alginate, potassium alginate, ammonium alginate and propylene glycol alginate, and wherein in the composition a concentration of the soluble alginate is 5 mg/mL-10 mg/mL.

2. The composition according to claim 1, wherein the soluble alginate is a mixture of sodium alginate and potassium alginate.

3. The composition according to claim 1, wherein the radionuclide includes at least one selected from the group consisting of iodine-131, iodine-125, phosphorus-32, yttrium-90, gallium-67, indium-111, thallium-201, palladium-203, bismuth-213, actinium-225, lutecium-177, rhenium-186, palladium-212 and rhenium-188.

4. The composition according to claim 1, wherein the radionuclide is iodine-131 or iodine-125.

5. The composition according to claim 1, wherein the concentration of the catalase is 5 mg/mL-10 mg/mL and the dose of the radionuclide is 200 Ci/mL-500 Ci/mL.

6. The composition according to claim 1, wherein the composition further comprises an immune-stimulating agent.

7. The composition according to claim 6, wherein the immune-stimulating agent includes at least one selected from the group consisting of CpG oligodeoxynucleotide which is a immunologic adjuvant, R837, TLR7 agonists, TLR8 agonists, NLR agonists, STING agonists, MPLA (Monophosphoryl Lipid A), LPS, PGNs, R848, G100, SD-101, MGN1703, CMP-001, FLA, polyU, poly(dT), CL307, CL264, CL097, CL075, MEDI9197, MEDI5083, hypoxanthine and MDP.

8. A method for preparing a composition comprising catalase, comprising mixing an alginate solution, a radionuclide and catalase.

9. The method according to claim 8, wherein a ratio of amount of the alginate solution, catalase, and radionuclide is 5 mg-10 mg: 5 mg-10 mg: 200 Ci-500 Ci.

10. The method according to claim 8, wherein the method of mixing includes mixing an alginate solution with a radionuclide-labeled catalase.

11. The method according to claim 10, wherein the radionuclide-labeled catalase is prepared by a method comprising mixing the radionuclide with an oxidizing agent and a dispersion medium, and mixing the obtained mixture with the catalase.

12. The method according to claim 10, wherein the radionuclide-labeled catalase is prepared by a method comprising mixing the catalase with a chelating agent, mixing the obtained mixture with the radionuclide and a reducing agent, and purifying.

13. The composition according to claim 1 for use in preparation of an anti-neoplastic agent.

14. The composition according to claim 13, wherein the composition is used in combination with at least one selected from the group consisting of an antibody against cytotoxic T-lymphocyte-associated antigen-4, anti-PD-1 and anti-PD-L1.

* * * * *